(12) United States Patent
Gavin et al.

(10) Patent No.: US 6,909,981 B2
(45) Date of Patent: Jun. 21, 2005

(54) DATA MANAGEMENT SYSTEM AND METHOD FOR PROCESSING SIGNALS FROM SAMPLE SPOTS

(75) Inventors: Edward J. Gavin, San Jose, CA (US); Cynthia Enderwick, San Jose, CA (US); Patrick Ho, Fremont, CA (US); Niels Kirk Thomsen, Santa Rosa, CA (US)

(73) Assignee: Ciphergen Biosystems, Inc., Fremont, CA (US)

( * ) Notice: Subject to any disclaimer, the term of this patent is extended or adjusted under 35 U.S.C. 154(b) by 0 days.

(21) Appl. No.: 10/754,461

(22) Filed: Jan. 8, 2004

(65) Prior Publication Data

US 2004/0159783 A1 Aug. 19, 2004

Related U.S. Application Data

(60) Provisional application No. 60/443,071, filed on Jan. 27, 2003.

(51) Int. Cl.[7] .............................................. G06F 19/00
(52) U.S. Cl. ......................................... 702/67; 250/340
(58) Field of Search ............................. 702/67, 22, 23, 702/27, 28, 35, 40, 83, 179, 182, 185, 189; 438/14, 16, 18; 250/340, 341.4, 341.8, 370.01

(56) References Cited

U.S. PATENT DOCUMENTS

| 6,225,047 | B1 |   | 5/2001 | Hutchens et al. |
|---|---|---|---|---|
| 6,584,413 | B1 | * | 6/2003 | Keenan et al. ................ 702/28 |
| 6,675,104 | B2 |   | 1/2004 | Paulse et al. |
| 2002/0054704 | A1 | * | 5/2002 | Smilansky et al. ......... 382/149 |
| 2002/0072982 | A1 | * | 6/2002 | Barton et al. ................. 705/26 |

* cited by examiner

*Primary Examiner*—Marc S. Hoff
*Assistant Examiner*—Edward Raymond
(74) *Attorney, Agent, or Firm*—Townsend and Townsend and Crew LLP

(57) ABSTRACT

One embodiment of the invention is directed to a method of processing a plurality of spectra. The method includes receiving values associated with a plurality of sample spots on one or more sample chips, wherein the values were entered using graphic elements representing the sample spots, the graphic elements being displayed on a graphical user interface. Data representing a plurality of signals are received. Each signal in the plurality of signals is annotated with a set of values associated with the sample spot from which the signal is generated.

25 Claims, 11 Drawing Sheets

DATA MANAGEMENT SYSTEM AND METHOD FOR PROCESSING SIGNALS FROM SAMPLE SPOTS

CROSS-REFERENCE TO RELATED APPLICATIONS

This application is a non-provisional of and claims the benefit of the filing date of U.S. Provisional Patent Application No. 60/443,071, filed on Jan. 27, 2003, which is herein incorporated by reference in its entirety.

BACKGROUND OF THE INVENTION

Proteins and other markers are important factors in disease states. A "marker" typically refers to a molecule such as a polypeptide, which alone or in combination with other markers, differentiates one biological state from another. For example, proteins can vary in association with changes in biological states such as disease. When disease strikes, some proteins become dormant, while others become active. Prostate Specific Antigen (PSA), for example, is a circulating serum protein that, when present in elevated concentrations, correlates with prostate cancer. When markers such as PSA are identified, they can be used as diagnostic tools or can be used to identify drugs that can be used to address the diseases associated with the markers.

Surface-enhanced laser desorption/ionization processes have been used to identify biomarkers. "Surface-enhanced laser desorption/ionization" or "SELDI" refers to a method of desorption/ionization gas phase ion spectrometry (e.g., mass spectrometry) in which an analyte (e.g., a protein) is captured at a sample spot of a SELDI probe that engages a probe interface of the gas phase ion spectrometer. In "SELDI MS," the gas phase ion spectrometer is a mass spectrometer. SELDI technology is described in, e.g., U.S. Pat. No. 5,719,060 (Hutchens and Yip) and U.S. Pat. No. 6,225,047 (Hutchens and Yip). A laser desorbs the captured analyte (e.g., a protein) from the surface of the probe and the desorbed analyte is received at a detector. A material called an "EAM" or energy absorbing material is at the sample spot and absorbs some of the laser energy during the desorption process.

After detection, the time of flight (TOF) of the desorbed analyte is determined. Each time-of-flight value is converted into a mass-to-charge ratio, or M/Z. TOF-to-M/Z transformation involves the application of an algorithm that transforms times-of-flight into mass-to-charge ratios (M/Z). In this step, the signals are converted from the time domain to the mass domain. After the proteins are desorbed and detected, and M/Zs are determined, a mass spectrum like the one shown in FIG. 1 is produced by the mass spectrometer.

As shown in FIG. 1, the y-axis is a measure of signal intensity while the x-axis represents a specific mass-to-charge ratio. A high signal intensity at a particular mass-to-charge ratio indicates a high concentration of a substance with that mass-to-charge ratio. In FIG. 1, the peak at about 27,000 represents a particular substance at that mass-to-charge ratio.

Spectra created under similar processing conditions can be separately grouped and then analyzed. For example, two mass spectra can be created using the same laser energy and wash conditions, but may be respectively derived from diseased and non-diseased samples. The two mass spectra may have different signal intensities (or "peaks") at a given mass-to-charge ratio. A substance at that particular mass-to-charge ratio can be characterized as being "differentially expressed" in the two samples, and the particular substance may be a marker for the particular diseased state that is being investigated.

Surface-enhanced laser desorption/ionization data is multi-dimensional and can include specific processing values such as type of energy absorbing material (EAM) used, the particular laser energy used, the type of adsorbent used, etc. One strength of the surface-enhanced laser desorption/ionization process includes the ability to identify markers such as proteins by analyzing a sample with a variety of different surface chemistries and different sample preparation steps.

With the increasing use of automated processing, even more spectra can be created than can be manually organized, processed, or analyzed by users. High throughput collection and analysis of such multi-dimensional surface-enhanced laser desorption/ionization data requires better data management systems than are presently available.

Embodiments of the invention address these and other problems.

SUMMARY OF THE INVENTION

Embodiments of the invention relate to systems and methods for processing spectra.

Another embodiment of the invention is directed to a method of processing a plurality of signals, the method comprising: (a) receiving values associated with a plurality of sample spots on one or more sample chips, wherein the values were entered using graphic elements representing the sample spots on a graphical user interface; (b) receiving data representing a plurality of signals, wherein the plurality of signals are generated from the sample spots; and (c) automatically annotating each signal in the plurality of signals with a set of values associated with the sample spot from which the signal is generated.

Another embodiment of the invention is directed to a computer readable medium comprising: (a) code for receiving values associated with a plurality of sample spots on one or more sample chips, wherein the values were entered using graphic elements representing the sample spots on a graphical user interface; (b) code for receiving data representing a plurality of signals, wherein the plurality of signals are generated from the sample spots; and (c) code for automatically annotating each signal in the plurality of signals with a set of values associated with the sample spot from which the signal is generated.

Another embodiment of the invention is directed to a system for processing mass spectra, the system comprising: (a) an analytical apparatus; and (b) a digital computer, the digital computer receiving data from the analytical apparatus, the digital computer comprising a computer readable medium including (i) code for receiving values associated with a plurality of sample spots on one or more sample chips, wherein the values were entered using graphic elements representing the sample spots on a graphical user interface; (ii) code for receiving data representing a plurality of signals, wherein the plurality of signals are generated from the sample spots; and (iii) code for automatically annotating, each signal in the plurality of signals with a set of values associated with the sample spot from which the signal is generated.

These and other embodiments of the invention are described in further detail below.

DETAILED DESCRIPTION

Figure 1:
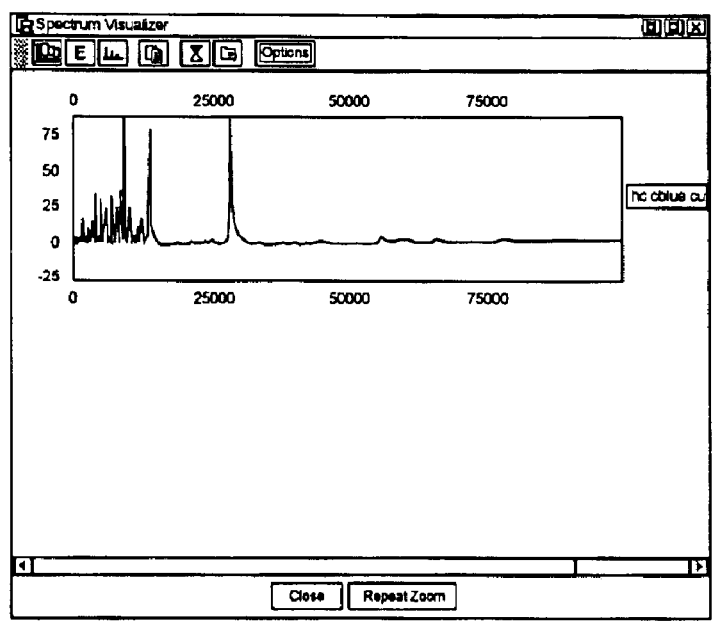
FIG. 1 shows a mass spectrum.

Embodiments of the invention can organize raw or processed spectra data, and track samples and processing parameters from the time an experiment is first designed to the time when the results of the experiment are analyzed. Each spectrum can be automatically annotated with values associated with the sample spot from which the spectrum was derived. This improves the speed and accuracy of later spectra analysis. An analysis module can provide advanced data handling and can include powerful data mining and analysis capabilities to allow for rapid, automated analysis of multiple experiments over multiple conditions to identify potential biomarkers. Embodiments of the invention can also be used to refine experimental results, generate reports, and publish findings.

A client-server, relational database architecture can be used in embodiments of the invention. A client server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications. Client computers rely on server computers for resources, such as files, devices, and even processing power. In some embodiments of the invention, the server computer handles all of the database functionality. The client computer can have software that handles all the front-end data management such as sorting, normalizing, and printing mass spectra. The client computer can also receive data input from users.

The digital computers (e.g., client computer, server computer) that are used in embodiments of the invention may include one or more micro, mini or large frame computers using any standard or specialized operating system such as a Windows™ or Linux™ based operating system.

The code for performing any of the functions described herein can be executed by the digital computers and may be stored on any suitable computer readable media. Examples of computer readable media include magnetic, electronic, or optical disks, tapes, sticks, chips, etc. The code for performing any of the functions described herein may also be written in any suitable computer programming language including, for example, Fortran, C, C++, etc. The graphical user interfaces and functions underlying the graphical user interfaces can be created using an object oriented programming language such as Java.

A method of processing a plurality of signals according to an embodiment of the invention includes (1) receiving values associated with a plurality of sample spots on one or more sample chips, wherein the values were entered using graphic elements representing the sample spots that are displayed on a graphical user interface; and (2) receiving data representing a plurality of signals, wherein the plurality of signals are generated from the sample spots. The values associated with the plurality of sample spots and the data representing the plurality of signals may be received at a digital computer such as a client computer or a server computer. After the data representing the plurality of signals and the values associated with the sample spots are "received" by the digital computer, (3) the digital computer can automatically annotate each signal in the plurality of signals with a set of values associated with the sample spot from which the signal is generated. As used herein, "receiving" includes the reception of data by a digital computer, microprocessor, or other computational apparatus.

Steps (1)–(3) above can be performed in different ways. For example, the values may be entered into a personal computer using a graphical user interface with graphic elements, and steps (1)–(3) may be performed by a microprocessor in the same personal computer. Alternatively, the values for the sample spots can be entered into a first computer such as a client computer using graphical elements. After the values are entered into the client computer, the value data may be transmitted to a server computer. The server computer may then perform steps (1)–(3).

Each sample spot has one or more "values" of a "characteristic" associated with it. A "characteristic" and a "value" of the characteristic may include information that relates to that sample spot. Suitable characteristics and values associated with those characteristics (in parentheses) can include, but are not limited to: wet lab processing parameters (e.g., wash solution A, wash solution B); energy absorbing material (e.g., sinapinic acid); fraction (e.g., fraction A, fraction B); adsorbent (e.g., adsorbent A, adsorbent B); sample type (e.g., blood, saliva); sample group (e.g., diseased, not diseased); laser energy (e.g., laser energy A, laser energy B); sample chip type (e.g., chip no. 1, chip no. 2), etc. In embodiments of the invention, a "fraction" is a particular portion of a sample that is obtained through a process such as chromatography. The different sample portions may comprise components within specific molecular weight, size, or charge ranges. For example, a sample such as blood can be processed through a chromatography column so that the blood is separated into different portions or "fractions". Each fraction can contain blood components within a specific range of molecular weights.

Any suitable analytical apparatus and method can be used to generate the signals that are associated with the sample spots. They can include, for example, gas phase ion spectrometry methods and apparatuses, optical methods and apparatuses, electrochemical methods and apparatuses, and atomic force microscopy and radio frequency methods and apparatuses. Of particular interest is the use of mass spectrometry and, in particular, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Immunoassays in various formats (e.g., ELISA) are popular methods for detecting analytes such as proteins captured on a solid phase. Electrochemical methods include voltametry and amperometry methods. Radio frequency methods include multipolar resonance spectroscopy.

In some embodiments, the signals are spectra. The spectra that are generated, manipulated, and analyzed in embodiments of the invention are preferably mass spectra. Each mass spectrum that is generated can be a plot of signal intensity vs. mass-to-charge ratio. Alternatively, each mass spectrum could simply comprise a table of signal intensity values and their corresponding M/Z values. Although "mass spectra" are described in detail in the examples below, it is understood that other types of spectra such as time-of-flight spectra could be annotated and processed in embodiments of the invention.

Specific exemplary methods according to an embodiment of the invention can be described with reference to FIGS. 2 and 3.

Figure 2:
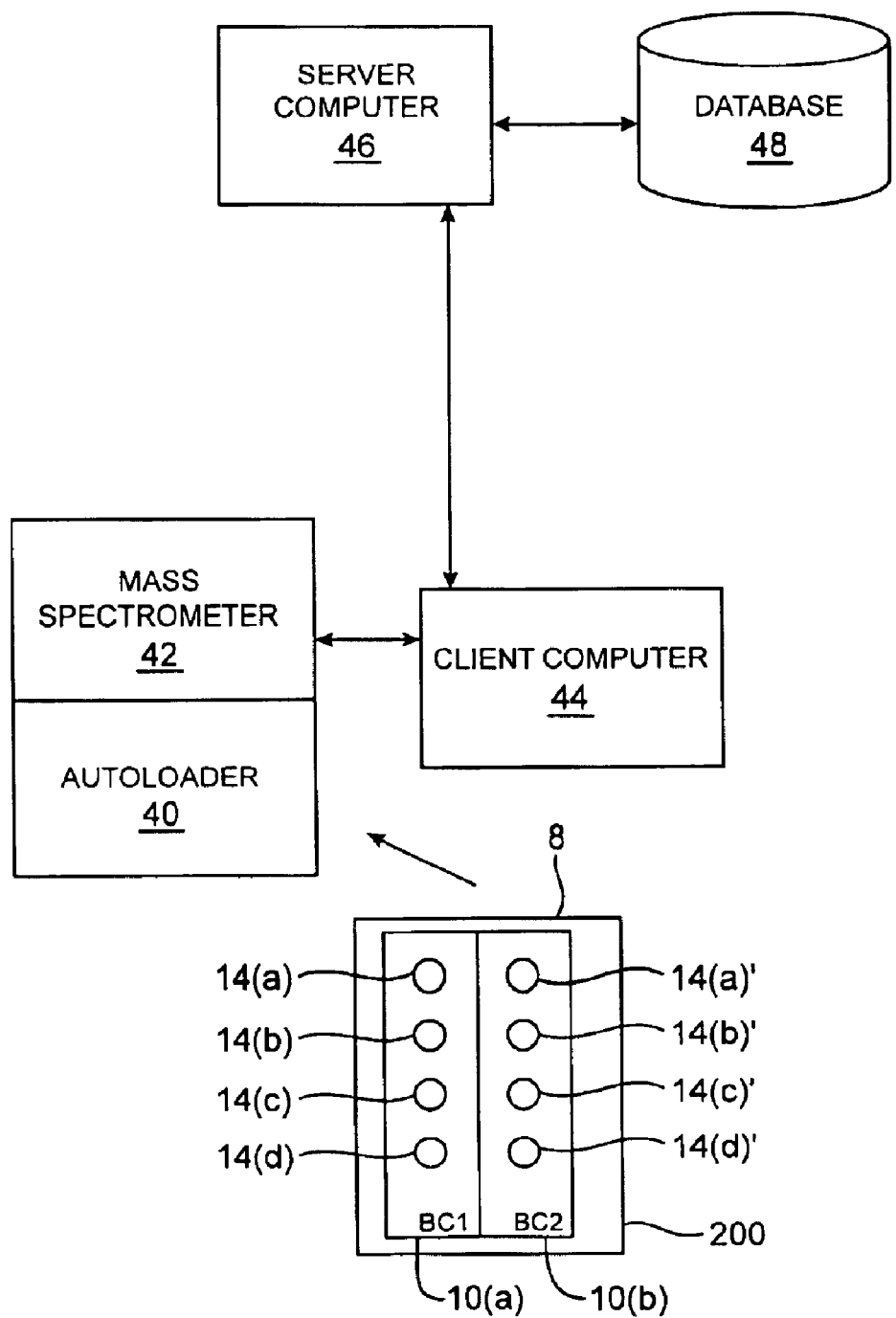
FIG. 2 shows a system according to an embodiment of the invention.

FIG. 2 shows a system according to an embodiment of the invention. FIG. 2 shows a client computer 44 that is in communication with a mass spectrometer 42. The client computer 44 may be structurally incorporated with the mass spectrometer 42, or may be a separate terminal such as a personal computer that is connected to the mass spectrometer 42. One client computer 44 is shown for simplicity of illustration. In other embodiments of the invention, there can be many client computers, and each client computer may or may not be coupled to a mass spectrometer.

In FIG. 2, an autoloader 40 is coupled to the mass spectrometer and can be used to automatically load a plurality of sample chips 10(a), 10(b) into the mass spectrometer 42. Each sample chip 10(a), 10(b) may include one or more sample spots 14(a)–14(d), 14(a)'–14(d)' and identifiers such as barcodes BC1, BC2. The sample chips 10(a), 10(b) may be secured in a holder 8. The combination of the holder 8 and the sample chips 10(a), 10(b), or the holder 8 itself may be referred to as a "bioprocessor" 200. Many bioprocessors and many sample chips may be automatically loaded into the mass spectrometer 42 with the autoloader 40 to produce at least one mass spectrum per sample spot 14(a)–14(d), 14(a)'–14(d)'.

The bioprocessor 200 may include any number of sample chips and each sample chip may include any suitable number of sample spots. As used herein, a "bioprocessor" includes a holder that holds one or more sample chips, each sample chip having one or more sample spots. In some embodiments, a bioprocessor 200 may hold 12 sample chips with 8 sample spots per sample chip for a total of 96 sample spots per bioprocessor. The sample spot configuration of the bioprocessor 200 can resemble that of a 96 well plate, which is a standard format for performing multiple assays. Bioprocessors that resemble a standard format such as the 96 well plate are useful, because they can be used with commercially available automated equipment. For example, a Biomek 2000 liquid handling robot (commercially available from Ciphergen Biosystems, Inc. of Fremont, Calif.), can pipette liquid samples into the wells of a 96 well plate or onto the sample spots that are in the bioprocessor.

A server computer 46 is in communication with the client computer 44 via a data network such as an intranet or the Internet. The server computer 46 may include one or more computational devices that receive data from and send data to the client computer 44 and other client computers. The server computer 46 may run an operating system such as Microsoft Windows™ 2000, may use a microprocessor such as an Intel based microprocessor (e.g., an Intel Pentium™ III 1 GHz or greater), and may have a CD ROM for program installation, and input and output devices for data input and output. It may have the following minimum characteristics: a memory capacity of 1 GB RAM or greater; and greater than 10 GB for program storage.

The client computer 44 may be a digital computer. The client computer 44 may run on a Windows 2000 or Windows XP operating system, and may have an Intel Pentium II 1 GHz or greater processor. It may also have a CDROM for program installation, and a mouse, keyboard, trackball, or any other suitable input device for data input, and visual and audio output devices for data output. It may have the following minimum characteristics: 256 MB RAM; 10 MB disk space for program data; and at least 1 GB of free disk space for data storage. The data requirements of the server computer 46 and the client computer 44 may change as processing speed and memory storage capacity increases in response to technological advances in computer technology.

The server computer 46 is in communication with a database 48, which can store spectra, values associated with the sample spots, or other data associated with the spectra or the process for forming the spectra. The database 48 may be a relational database that is commercially available from Oracle or MySQL. Relational databases store data in the form of related tables. Relational databases are powerful because they require few assumptions about how data is related or how it will be extracted from the database. As a result, the same database can be viewed in many different ways. A useful feature of a relational database is that it can be spread across several tables. Any number of users may access the database 48 to retrieve stored spectra (annotated or unannotated), or values associated with the sample spots.

The mass spectrometer 42 may use any suitable ionization technique to create spectra. The ionization techniques may include, for example, an electron ionization, fast atom/ion bombardment, matrix-assisted laser desorption/ionization (MALDI), surface enhanced laser desorption/ionization (SELDI), or an electrospray ionization process.

In some embodiments, an ion mobility spectrometer can be used. The principle of ion mobility spectrometry is based on the different mobility of ions. Specifically, ions of a sample produced by ionization move at different rates due to their difference in, e.g., mass, charge, or shape, through a tube under the influence of an electric field. The ions are received at a detector and the output of the detector can then be used to identify a marker or other substances in a sample.

One advantage of ion mobility spectrometry is that it can be performed at atmospheric pressure.

In preferred embodiments, a laser desorption time-of-flight mass spectrometer is used to create the mass spectra. Laser desorption spectrometry is especially suitable for analyzing high molecular weight substances such as proteins. For example, the practical mass range for a MALDI or a surface enhanced laser desorption/ionization process can be up to 300,000 daltons or more. Moreover, laser desorption processes can be used to analyze complex mixtures and have high sensitivity. In addition, the likelihood of protein fragmentation is lower in a laser desorption process such as a MALDI or a surface enhanced laser desorption/ionization process than in other mass spectrometry processes. Thus, laser desorption processes can be used to accurately characterize and quantify high molecular weight substances such as proteins.

Figure 3:
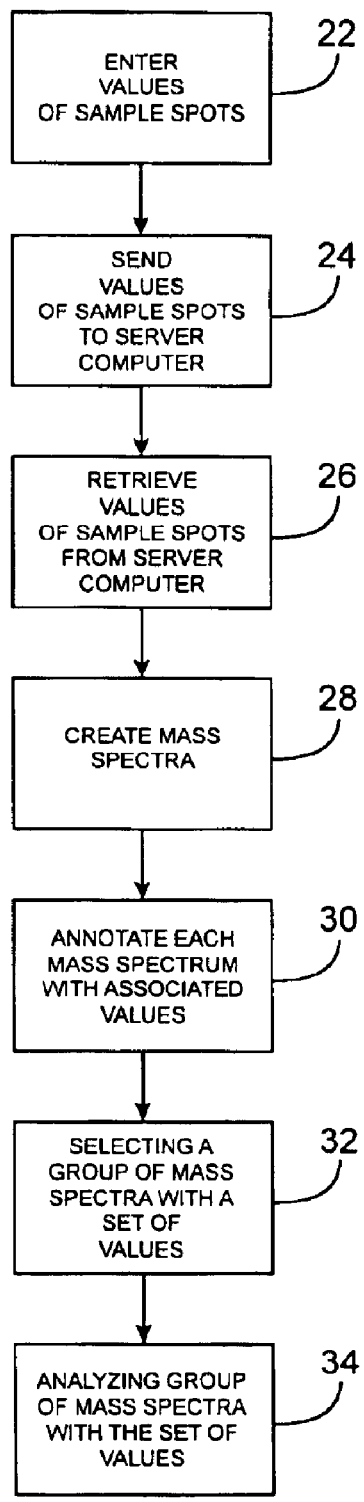
FIG. 3 shows a flowchart showing a method according to an embodiment of the invention.

FIG. 3 shows a flowchart of a method according to an embodiment of the invention. First, a user enters values associated with the sample spots on one or more sample chips into a client computer via a graphical user interface that contains graphic elements representing the sample spots on the sample chips (step 22). After they are entered into the client computer, values associated with those sample spots can be sent from the client computer to a server computer (step 24). The server computer stores the received values in the database. Sample spots on one or more sample chips can be prepared according to the values that were previously entered by the user. Prior to or after creating mass spectra, the values for the sample spots can then be retrieved from the server computer (step 26) and received at the client computer (or on a different client computer). The mass spectrometer can analyze the samples on the sample spots, and spectra data can be created or received by the client computer (step 28). The client computer can automatically annotate each mass spectrum with the values of the sample spot from which the mass spectrum was created (step 30). Once the mass spectra are annotated, a group of mass spectra with a set of the previously entered values are selected (step 32). At any point in the process, the spectra (in annotated or unannotated form) may be sent back to the server computer for storage or processing. The selected group of mass spectra can then be analyzed using an analytical module (step 34). The analytical module can be present on the client computer or server computer, and can analyze the selected spectra. For example, the analytical module may perform, for example, a differential expression analysis, or a recursive partitioning analysis on the selected group of mass spectra. Each of these steps is described in further detail below with reference to FIGS. 2–17.

A user may design an experiment by entering different values for one or more sample spots into a digital computer. Referring to FIGS. 2 and 3, values for each of the sample spots 14(a)–14(d), 14(a)'–14(d)' on one or more sample chips 10(a), 10(b) are entered into the client computer 44 (step 22). Each sample spot 14(a)–14(d), 14(a)'–14(d)' can have zero, one, or two or more values associated with it. For example, each sample spot may have a different wash condition, a different sample, and a different laser energy associated with it. Each sample spot 14(a)–14(d), 14(a)'–14(d)' can also be used to generate one or more spectra. If a single bioprocessor contains 96 sample spots total, at least 96 spectra could be respectively generated from those 96 spots. In practice, there may be many bioprocessors with many sample chips, each sample chip having many different sample spots. The number of spectra that can be generated is large, thus providing a need for more efficient and useful spectra data management systems and methods.

Each sample spot may contain a biological sample. Any suitable biological samples may be used in embodiments of the invention. Biological samples include tissue (e.g., from biopsies), blood, serum, plasma, nipple aspirate, urine, tears, saliva, cells, soft and hard tissues, organs, semen, feces, urine, and the like. The biological samples may be obtained from any suitable organism including eukaryotic, prokaryotic, or viral organisms.

The biological samples may include biological molecules including macromolecules such as polypeptides, proteins, nucleic acids, enzymes, DNA, RNA, polynucleotides, oligonucleotides, nucleic acids, carbohydrates, oligosaccharides, polysaccharides; fragments of biological macromolecules set forth above, such as nucleic acid fragments, peptide fragments, and protein fragments; complexes of biological macromolecules set forth above, such as nucleic acid complexes, protein-DNA complexes, receptor-ligand complexes, enzyme-substrate, enzyme inhibitors, peptide complexes, protein complexes, carbohydrate complexes, and polysaccharide complexes; small biological molecules such as amino acids, nucleotides, nucleosides, sugars, steroids, lipids, metal ions, drugs, hormones, amides, amines, carboxylic acids, vitamins and coenzymes, alcohols, aldehydes, ketones, fatty acids, porphyrins, carotenoids, plant growth regulators, phosphate esters and nucleoside diphospho-sugars, synthetic small molecules such as pharmaceutically or therapeutically effective agents, monomers, peptide analogs, steroid analogs, inhibitors, mutagens, carcinogens, antimitotic drugs, antibiotics, ionophores, antimetabolites, amino acid analogs, antibacterial agents, transport inhibitors, surface-active agents (surfactants), mitochondrial and chloroplast function inhibitors, electron donors, carriers and acceptors, synthetic substrates for proteases, substrates for phosphatases, substrates for esterases and lipases and protein modification reagents; and synthetic polymers, oligomers, and copolymers. Any suitable mixture or combination of the substances specifically recited above may also be included in the biological samples.

Figure 4:
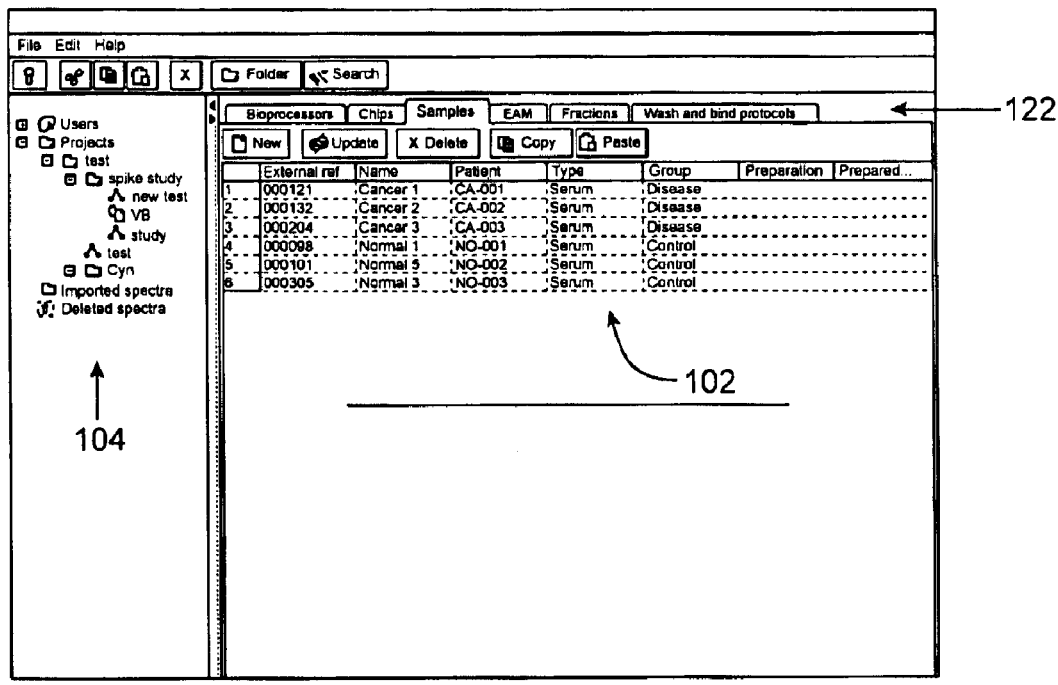
FIG. 4 shows a graphical user interface where a user can input sample data.

FIG. 4 shows a graphical user interface that can be displayed on the client computer. The graphical user interface includes a window 104 that displays a tree that can be used to browse the data that has been stored in the system. There are several general entities that can represent a leaf in the tree. A "folder" can be a general container for spectra, virtual notebooks, and studies. Folders can act as branches and can contain other folders. Multiple folders, studies, and virtual notebooks can exist in each folder. A "virtual notebook" contains sample property information and sample chip or bioprocessor configurations. Virtual notebooks are described in further detail below. An "analysis folder" can contain analysis data. Spectra can be inserted into an analysis folder via a query tool. An "imported spectra folder" can accept spectrum data acquired from an external source, such as ProteinChip Software 3.1.1 (or later versions), which is commercially available from Ciphergen Biosystems, Inc. of Fremont, Calif. The "deleted spectra folder" holds deleted spectra.

In embodiments of the invention, a user can use a "virtual notebook" to enter values associated with the sample spots into the client computer. The "virtual notebook" is an electronic or "virtual" representation of a laboratory notebook where a user can track and enter sample spot values such as a sample name, a particular sample type, a particular EAM used, a particular fraction, a particular bind and wash condition, etc. It can include a graphical user interface with graphic elements that are graphical representations of the sample spots on a sample chip or in a bioprocessor. The graphical user interface allows a user to apply a set of sample spot values to many sample spots on one or more sample chips or one or more bioprocessors in a few steps. Values of characteristics such as wet lab processing conditions can be applied "virtually" to the representations of the sample spots.

When a user uses the virtual notebook, there can be a series of tabs from which the user may select to "configure" one or more sample chips, or a bioprocessor containing the sample chips, according to a particular experimental procedure. Tabs that the user can select from can be provided on a graphical user interface. Each tab can represent a list of preconfigured elements of a bioprocessor. For example, the tabs may correspond to: bioprocessors, arrays, samples, EAM, fractions, and wash and bind protocols. Each tab contains a list of preconfigured elements (if any) that have been added to the virtual notebook for use in a bioprocessor. For example, the EAM tab contains a list of specific EAMs along with the buttons to enter more EAMs, or delete unneeded ones. Also, these elements can be copied and pasted from other virtual notebooks in the system.

The data table 102 shown on the right hand side of the window shown in FIG. 4 shows different sample information that can be entered into the client computer 44. The sample information can be entered into the client computer 44 by selecting the "samples" tab. The sample information may include, for example, an external reference code, a name (e.g., cancer 1), a patient (e.g., CA-001), a sample type (e.g., serum), and a particular group (e.g., disease, control) associated with the sample.

In an exemplary embodiment, a new spectrum that is generated from a sample spot that is tracked in the virtual notebook will have the specific set of values that is associated with it. The mass spectrum can be automatically annotated with the values for the sample spot. For example, a new mass spectrum may have been created from a sample spot on a chip type X containing a blood sample from a diseased patient and a sinapinic acid EAM, while using a laser energy of Y. The values (i.e., chip type X, blood, diseased, sinapinic acid, laser energy=Y) of that sample spot can be annotated to the new mass spectrum. In the virtual notebook, each value is tracked within its own data table so that each value can be applied to different sample spots on different sample chips and bioprocessors. The virtual notebook streamlines the procedure to configure one or more sample spot arrays on one or more sample chips, by allowing a user to characterize multiple sample spots on several arrays at a time.

A "wizard", like those commonly used in many Windows™ operating environments, may be provided to prompt and guide the user in configuring the sample spots in the sample chips and the bioprocessor in the virtual notebook. The wizard can first ask for information about the bioprocessor or the sample chips. The wizard allows the user to add sample spot arrays, and values for sample spot characteristics such as samples, fractions, bind and washes, and EAMs to each sample spot. The sample spots can form a map, which is laid out to match the layout of either the sample spots in the actual bioprocessor or sample chips being configured. For example, a simple table appears to holds information for up to 12 arrays. Each column of the table represents an array of a sample chip. The sample spots are shown in the same order as they would lie in the actual bioprocessor or on the sample chip used. A user may use a mouse or other input device to point and click to specific values and then these values can be applied to the representations of the sample spots. The sample spots can be color coded according to the different sample groups of the samples that are applied to the sample spots.

Figure 5:
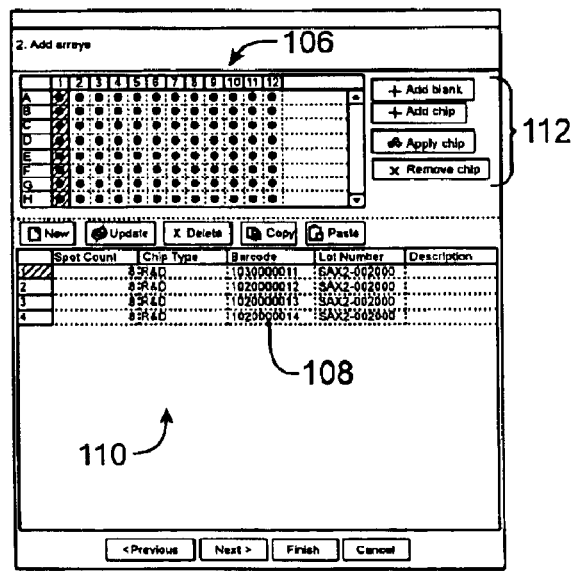
FIG. 5 shows a graphical user interface showing an array of graphic elements representing a plurality of sample spots on chips in a bioprocessor.

Illustratively, the virtual notebook may include a graphical user interface like the one shown in FIG. 5. The values of the different sample spots on one or more sample chips can be entered into the client computer 44 using a graphical user interface such as the one shown in FIG. 5. FIG. 5 shows graphic elements 106 that are graphical representations of a plurality of sample spots on a plurality of sample chips. In this example, there are representations for 12 sample chips labeled 1 through 12, and each sample chip has sample spots A–H. The 12 sample chips that are illustrated represent 12 sample chips in a single bioprocessor. The bioprocessor may comprise a holder and the 12 chips. In this example, the bioprocessor has 12 chips with 8 sample spots each for a total of 96 sample spots. The 96 sample spots can be in a configuration that is similar to a 96 well plate.

In this example, the graphic elements 106 are graphically represented by round circles that are similar in general appearance to the sample spots on the sample chips in the bioprocessor. However, in other embodiments, the graphic elements can be different. For example, the graphical elements could be numbers, letters, or other symbols in other embodiments.

Referring again to FIG. 2, each sample chip 10(a), 10(b) and/or bioprocessor 200 is identified to the client computer 44 using a barcode BC1, BC2 or other identifier. A user may either type in the barcode number or use a barcode scanner to enter the sample chip identifier into the client computer and into the system. Referring to FIG. 5, as shown in the data table 110, each sample chip has a bar code number associated with it 108.

Other information such as spot count, chip type, and lot number can be input into the data table 110. Alternatively, the spot count and chip type are automatically filled in based on a lookup table that associates the first three digits of a barcode with the chip type and format (the physical layout of a sample chip with the spot count). These data fields may be read-only. Buttons 112 are provided so that a user can add a blank, add a chip, apply selected conditions to a chip, or remove a chip. Accordingly, when configuring a bioprocessor, the number of sample spots that are used in the bioprocessor and the values associated with those sample spots can be changed.

Figure 6:
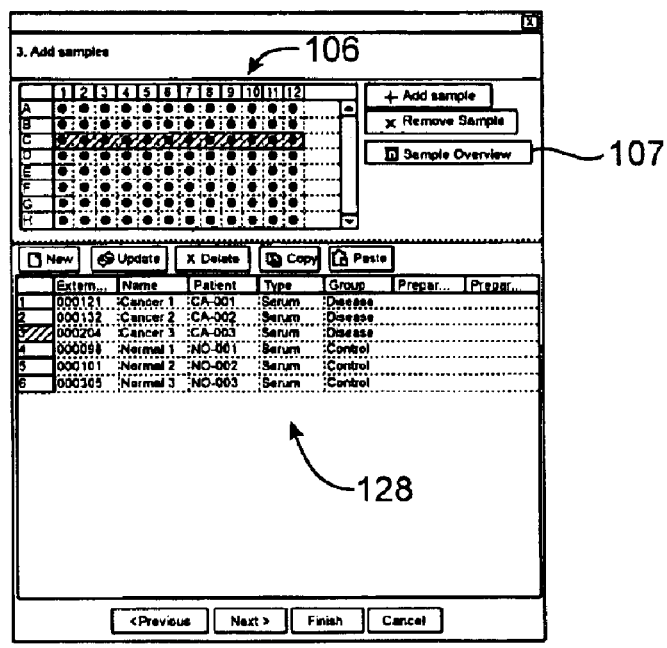
FIG. 6 shows a graphical user interface showing an array of graphic elements and sample data.
Figure 7:
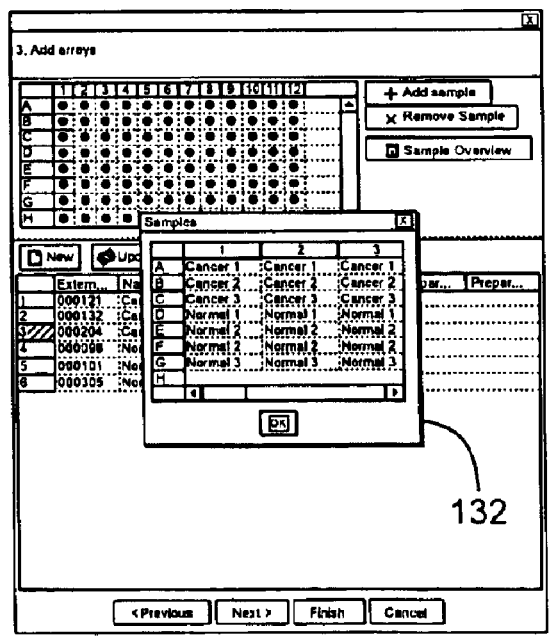
FIG. 7 shows the graphical user interface shown in FIG. 6 with another window showing an array of sample types.

Referring to FIG. 6, samples may be applied to a selected group of the sample spots 106. To add a sample to a selected group of sample spots, the "Add sample" button can be selected. For example, one of the samples shown in the sample table 128 can be selected and it can be applied to the sample spots. The sample table 128 shows six samples that the user can select from. For example, the user can select sample "3" using an input device such as a mouse or keyboard, and the user can highlight the sample spots at position "C" on each of sample chips 1–12. The user may then select the "Add sample" button to add sample 3 to sample spot C on each of the sample chips in the bioprocessor. The sample 3 is added to the sample spots C "virtually". At a later time, the instruction to add sample 3 to sample spots C in sample chips 1–12 in the bioprocessor can be carried out by an automated sample handling machine such as a multichannel pipette tool, which will automatically apply sample 3 to sample spots C in the actual bioprocessor.

A "sample overview" button 107 is also shown in FIG. 6. After selecting the "sample overview" button 107, a window such as the window 132 shown in FIG. 7 can be displayed to the user. This allows a user to see the different samples that are applied to the different sample spots on the chips in the bioprocessor. In the illustrated example, there are 3 cancer samples and 3 normal samples and these samples are applied on different sample spots on different chips in the bioprocessor.

Figures 8, 9:
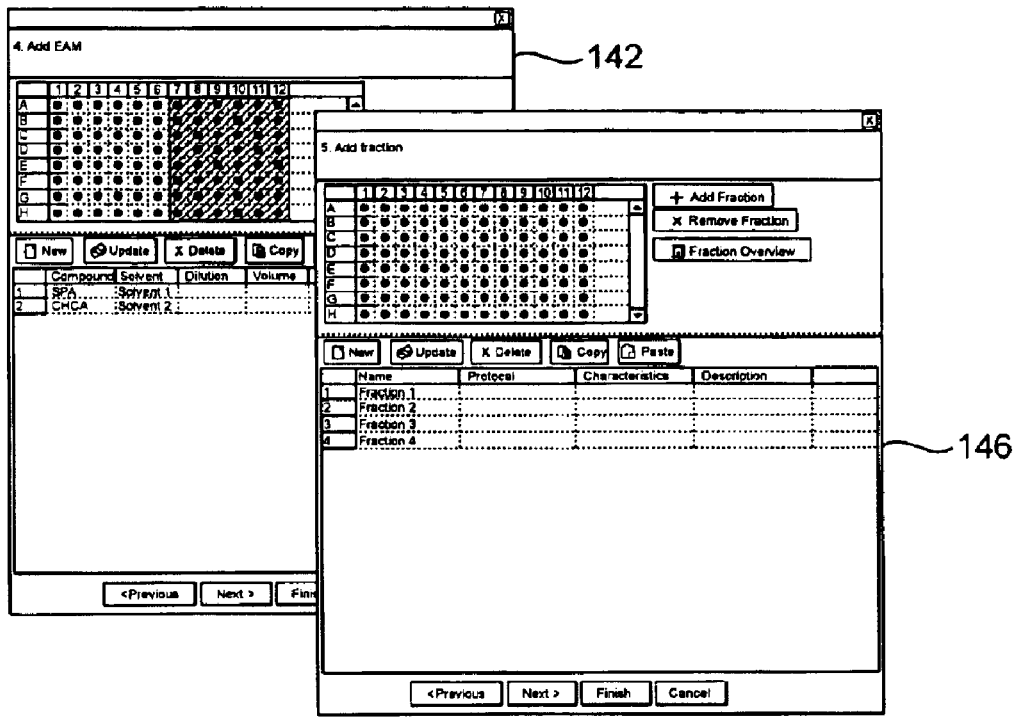
FIG. 8 shows a first window with an array of graphic elements and EAMs that can be selected, and a second window with an array of graphic elements and fractions that can be selected.
FIG. 9 shows a data array showing the different values associated with the different sample spots in an array of sample spots.

As shown in FIG. 8, EAM and sample fraction values can be added to the sample spots in the same manner as described above for each of the different samples.

FIG. 9 shows a bioprocessor overview screen. This screen provides a tabular, at-a-glance view of the experimental layout of the bioprocessor. This view may be printed for reference. After the bioprocessor has been configured, the user may display an overview of it by selecting the bioprocessor tab (see FIG. 4), selecting the bioprocessor of interest, and then selecting an "Overview" button. After selecting this button, the overview of the bioprocessor may be presented in table or chart form. As shown in FIG. 9, the values of the characteristics of the different sample spots in the bioprocessor are listed for the user.

Advantageously, using embodiments of the invention, experiments can be easily designed before mass spectra are created. The experimental data such as the data that is in the experimental layout in FIG. 9 may be automatically added to sample spots in a plurality of sample chips using automatic processing equipment and mass spectra may be automatically generated (e.g., using automated pipetting tools, automated chip or bioprocessor handlers, and automated mass spectrometers). The values for the sample spots can be saved for later annotation of the mass spectra that are formed from the sample spots. In addition, it is apparent that the data entry process that is described above is more intuitive for the user than manually annotating each mass spectrum produced. Embodiments of the invention are therefore easier for a user to use than conventional annotation processes.

Referring again to FIGS. 2–3, after the values of the sample spots on the sample chip are entered into the client computer 44, the values of the sample spots are sent to a server computer 46 (step 24). The entered values are then stored in a database 48 that is accessible to the server computer 46. For example, the data shown in the experimental layout 10 shown in FIG. 9 can be sent to the server computer 46 and can be stored in the database 48. The database 48 can also store raw or processed mass spectra data, as well as the annotated mass spectra that are eventually produced.

Using the central server computer 46 and the database 48 to store the entered sample spot values, and annotated and unannotated mass spectra is advantageous. For example, hundreds or even thousands of mass spectra could be rapidly generated using automated processing techniques. The numerous mass spectra are very data intensive, and are difficult to process and analyze using a typical client computer. It is therefore desirable to have the mass spectra and values associated with the mass spectra stored at a central database 48 with large data storage capacity to reduce the memory requirements of the multiple client computers that may be in the data network that is used. In addition, by using a centralized server computer 46 and database 48, others may share the mass spectra information more readily than if each user is using his or her own client computer to process and store mass spectra data.

When the sample chips 10(a), 10(b) are ready to be processed by a mass spectrometer 42, a scanner (not shown) coupled to the client computer 44, the mass spectrometer 42 and/or the autoloader 40, automatically reads the barcodes BC1, BC2 or other identifiers on the sample chips 10(a), 10(b).

Using the barcodes BC1, BC2, the particular values for sample spots 14(a)–14(d), 14(a)'–14(d)' on the sample chips 10(a), 10(b) are retrieved using the server computer 46 (step 26). Before acquisition, the software controlling the mass spectrometer reads the barcodes BC1, BC2 on the sample chips 10(a), 10(b). The software on the client computer 44 sends a request such as a SOAP request to the server computer 46 with the barcode information BC1, BC2. (SOAP stands for Simple Object Access Protocol and is a messaging protocol that uses HTTP as the base transport and XML as the method for encoding invocation requests and responses to access services, objects, and servers in a platform-independent manner.) The server computer 46 sends the previously entered sample values for the sample spots 14(a)–14(d), 14(a)'–14(d)' back to the client computer 44.

Before or after the values are retrieved from the server computer 46, the mass spectrometer 42 creates mass spectra from samples that are on the sample spots 14(a)–14(d), 14(a)'–14(d)' (step 28). In a typical process for creating a mass spectrum, a sample chip is introduced into an inlet system of the mass spectrometer. Substances such as proteins in a sample on the sample chip are then ionized. After the ions are generated, the generated ions are collected by an ion optic assembly, and then a mass analyzer disperses and analyzes the passing ions. The ions exiting the mass analyzer are detected by a detector. In a time-of-flight mass analyzer, ions are accelerated through a short high voltage field and drift into a high vacuum chamber. At the far end of the high vacuum chamber, the accelerated ions strike a sensitive detector surface at different times. Since the time-of-flight of the ions is a function of the mass-to-charge ratio of the ions, the elapsed time between ionization and impact can be used to identify the presence or absence of molecules of specific mass-to-charge ratio.

After the mass spectra are produced by the mass spectrometer 42, they can be automatically processed by appropriate software in the client computer 44 that is coupled to the mass spectrometer 42. Spectra processing methods may include baseline subtraction, filtering, peak detection, spot corrected calibration, and optionally normalization. These processes are described in further detail below.

Also, after the mass spectrometer 42 creates the mass spectra, the client computer 44 annotates each mass spectrum (step 32) with the values associated with the sample spot from which the mass spectrum is created. Once annotated, each annotated mass spectrum can then be sent back to the server computer 46 for storage in the database 48 or for storage in a memory device in the client computer 42.

"Annotating" a mass spectrum can refer to correlating the values for the sample spot that was used to create the mass spectrum with the mass spectrum data. The mass spectrum data could be in graphical form (as in a plot of signal intensity vs. M/Z) or could be in tabular form. For example, values such as EAM=sinapinic acid, sample=cancer 1, and chip-type=X may be linked to mass spectrum data that is derived from the sample spot having these values.

After acquisition, each spectrum is saved in an XML file format containing all the stored values received from the server computer 46. This enables each mass spectrum to be its own entity, ready to be loaded into any server computer, including the one it originated from. The mass spectrum XML file can contain raw TOF data, un-normalized (or normalized) processed data (according to the parameters set up in a previous step), calibrated and spot-corrected masses (if spot-correction is enabled), sample property information, processing parameters such as filtering and baseline parameters, and acquisition information. Checksums can be calculated for the raw TOF data, the processed data, and the entire file to ensure that the TOF data has not been altered during the transfer of data between a client computer and a server computer. A spot-correction factor can also saved in the file.

The annotated spectra may then be loaded into the database 48 by the server computer 46. The spectrum files may be saved to a particular folder on the database 48. When manually loading spectra, one is able to designate the folder in which the spectra reside. When auto-loading, the spectra can be stored in a default folder on the database 48. When automatically sending spectra to the server computer (e.g., via an http post), the folder names can be sent along with the post to indicate where the spectra are to be stored in the database 48. For example, if the string "BDC project\Q103\Replicate analysis" was sent with an http post, a hierarchy of folders will be created in the database 48. The folder "BDC project" will contain "Q013" which will contain "Replicate analysis".

After the mass spectra are annotated, each mass spectrum may be further processed. For example, algorithms may be applied to the mass spectra to improve them in some way or to identify peaks of interest. Such algorithms may perform TIC (total ion current) normalization, calibration, peak identification, baseline subtraction, and filtering.

Normalization is the process of linearly scaling the numbers in a data set to account for spectrum-to-spectrum variations due to different conditions and improve the accuracy of the subsequent numeric computations. Normalizing by total ion current is useful when studying spectra that have been produced on different days, or on different instruments. The normalization process takes the total ion current used for all the sample spots, averages the intensities, and adjusts the intensity scales for all the sample spots so that the data that are displayed are on the same scale.

Calibration processes calibrate for systematic errors in the mass spectrometry process. Calibration can be done internally or externally. In internal calibration, the sample being analyzed contains one or more samples of known M/Z. The differences between the obtained M/Zs for the known samples can be used to correct M/Zs for unknown samples. In external calibration, a function that converts times-of-flight to M/Z ratios, such as one created by prior internal calibration, is applied to a time-of-flight spectrum without the use of internal calibrants. Exemplary calibration methods are described in U.S. patent application Ser. No. 10/194,452, filed on Jul. 11, 2002, and entitled "Method for Calibrating a Mass Spectrometer."

Peak identification processes such as those that are used in Ciphergen's ProteinChip® software can automate the detection of peaks and can be used in embodiments of the invention. In general, this software functions by identifying signals having a signal-to-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster. Exemplary peak identification methods are described in U.S. patent application Ser. No. 10/084,587, filed on Nov. 15, 2001, and Ser. No. 09/999,081, filed on Nov. 15, 2001, each of which is entitled "Method For Analyzing Mass Spectra."

A baseline subtraction process can also be performed on the mass spectra data. A baseline subtraction process improves data quantification by eliminating artificial, reproducible instrument offsets that perturb the spectrum. It involves calculating a spectrum baseline using an algorithm that incorporates parameters such as peak width, and then subtracting the baseline from the mass spectrum.

The mass spectra data could also be filtered. High frequency noise signals are eliminated by the application of a smoothing function. A typical smoothing function applies a moving average function to each time-dependent bin. In an improved version, the moving average filter is a variable width digital filter in which the bandwidth of the filter varies as a function of, e.g., peak bandwidth, generally becoming broader with increased time-of-flight. See, e.g., WO 00/70648, Nov. 23, 2000 (Gavin et al., "Variable Width Digital Filter for Time-of-flight Mass Spectrometry").

Figure 10:
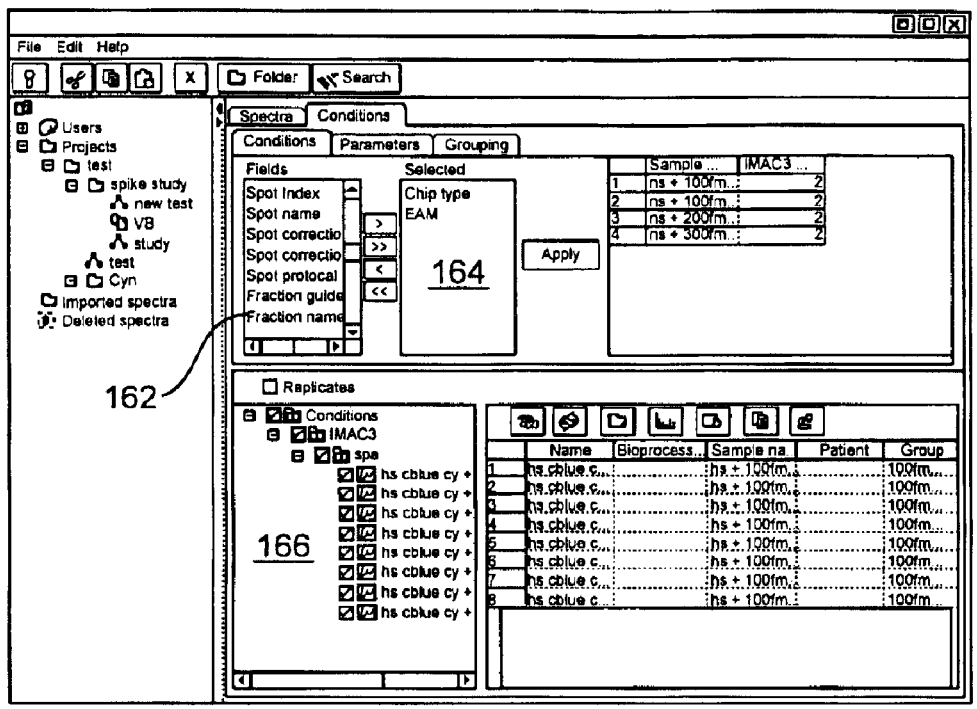
FIG. 10 shows a graphical user interface which allows a user to group spectra according to selected values.

In some embodiments, the spectra are grouped together into a study by querying the database for spectra meeting query conditions in order to "analyze" (e.g., automatically) the mass spectra. As used herein, "analyze" includes analyzing or processing the mass spectra in any suitable manner to obtain or attempt to obtain useful information from the spectra. For example, the mass spectra may be analyzed to discover potential markers. In another example, the mass spectra may be analyzed to form a classification model, and/or may be analyzed to classify the spectra (and the samples corresponding to them) according to a particular class (e.g., diseased or normal). For example, these conditions may be based on folder, time of acquisition, user, array type, sample type, patient, group, etc. In order to compare spectra under similar processing conditions, a group of mass spectra may be selected with a predetermined set of values (step 32 in FIG. 3). As shown in FIG. 10, the user may select common characteristics from many different data fields 162 and these selected characteristics may be displayed in the window 164. As shown in window 166, the eight spectra that are created using the chip type "IMAC3" and the EAM (energy absorbing material) SPA (sinapinic acid) are grouped together.

Referring again to FIGS. 2–3, after selecting a group of mass spectra with the predetermined set of values, the grouped spectra may be analyzed (step 34). For example, the grouped spectra may be analyzed using a statistical process to determine if they reveal potential biomarkers that differentiate different sample groups that are associated with the spectra. The code for performing these steps may be present in an analysis module that is present on the client computer 44 or the server computer 46.

In some embodiments, the analysis module can apply analysis algorithms to the selected and grouped mass spectra data. An analysis module can use analysis processes such as hierarchical clustering, p-value plots, and multi-condition visualizations.

Statistical processes such as recursive partitioning processes can also be used to classify spectra. The spectra that are grouped together can be classified using a pattern recognition process that uses a classification model. In general, the spectra will represent samples from at least two different groups for which a classification algorithm is sought. For example, the groups can be pathological v. non-pathological (e.g., cancer v. non-cancer), drug responder v. drug non-responder, toxic response v. non-toxic response, progressor to disease state v. non-progressor to disease state, phenotypic condition present v. phenotypic condition absent.

In some embodiments, data derived from the spectra (e.g., mass spectra or time-of-flight spectra) that are generated using samples such as "known samples" can then be used to "train" a classification model. A "known sample" is a sample that is pre-classified. The data that are derived from the spectra and are used to form the classification model can be referred to as a "training data set". Once trained, the classification model can recognize 30 patterns in data derived from spectra generated using unknown samples. The classification model can then be used to classify the unknown samples into classes. This can be useful, for example, in predicting whether or not a particular biological sample is associated with a certain biological condition (e.g., diseased vs. non diseased).

The training data set that is used to form the classification model may comprise raw data or pre-processed data. In some embodiments, raw data can be obtained directly from time-of-flight spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, which is herein incorporated by reference in its entirety.

In supervised classification, training data containing examples of known categories are presented to a learning mechanism, which learns one more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as backpropagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are in U.S. Provisional Patent Application Nos. 60/249,835, filed on Nov. 16, 2000, and 60/254,746, filed on Dec. 11, 2000, and U.S. Non-Provisional patent application Ser. No. 09/999,081, filed Nov. 15, 2001, and Ser. No. 10/084,587, filed on Feb. 25, 2002. All of these U.S. Provisional and Non Provisional Patent Applications are herein incorporated by reference in their entirety for all purposes.

In other embodiments, the classification models that are created can be formed using unsupervised learning methods. Unsupervised classification attempts to learn classifications based on similarities in the training data set, without pre classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Figure 11:
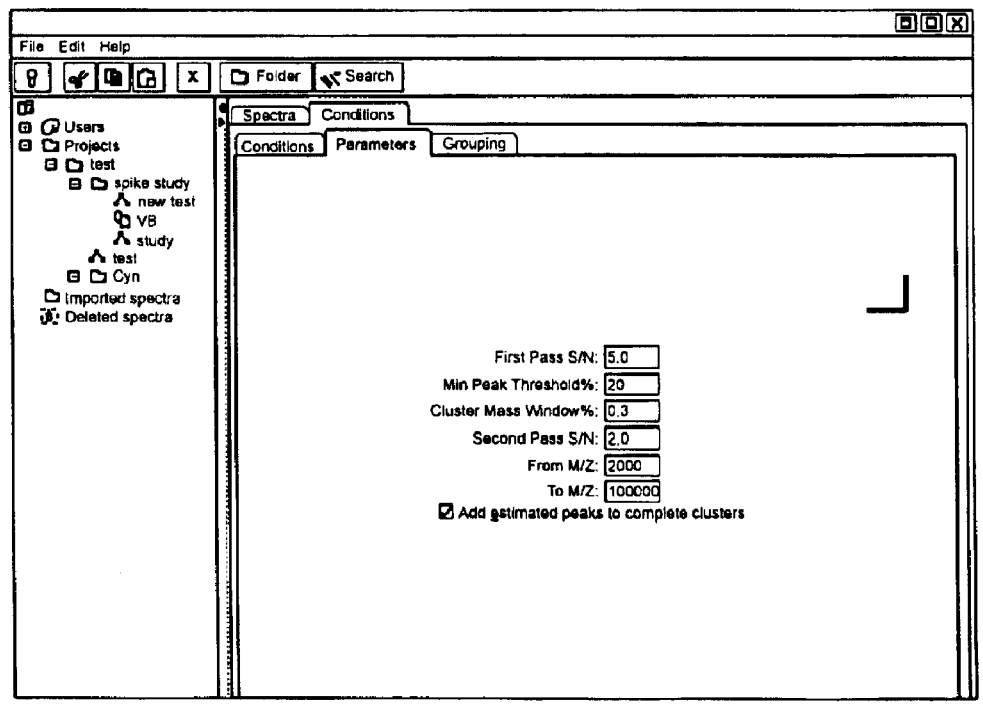
FIG. 11 shows a user interface that a user can use to select clusters of peaks in a plurality of mass spectra according to predetermined criteria.

Other signal processing steps can be performed on the grouped mass spectra by a signal processing module to help identify peaks of interest in the grouped mass spectra. For example, FIG. 11 shows a graphical user interface where a user can enter a first pass signal-to-noise ratio, a minimum peak threshold %, a cluster mass window %, a second pass S/N ratio, or a particular M/Z range. It can also allow a user to add estimated peaks to complete clusters. "First Pass S/N" allows a user to specify the sensitivity of the first pass of peak detection. The higher the number, the smaller the number of peaks that are detected. "Min. Peak Threshold %" allows a user to specify the percentage of spectra in which a peak must appear in order to form a cluster. "Cluster Mass Window %" allows a user to specify the width of a cluster mass window. "Second Pass S/N" allows a user to instigate a second pass of peak detection so that smaller peaks can be added to an existing cluster. The sensitivity of the second pass can be adjusted by changing the minimum signal-to-noise value. "From M/Z" allows a user to specify the starting mass of the second pass. "To M/Z" allows a user to specify an ending mass of the second pass. "Add estimated peaks to complete clusters" allows a user to add estimated peaks to spectra that do not already have a peak within a given cluster.

Figure 12:
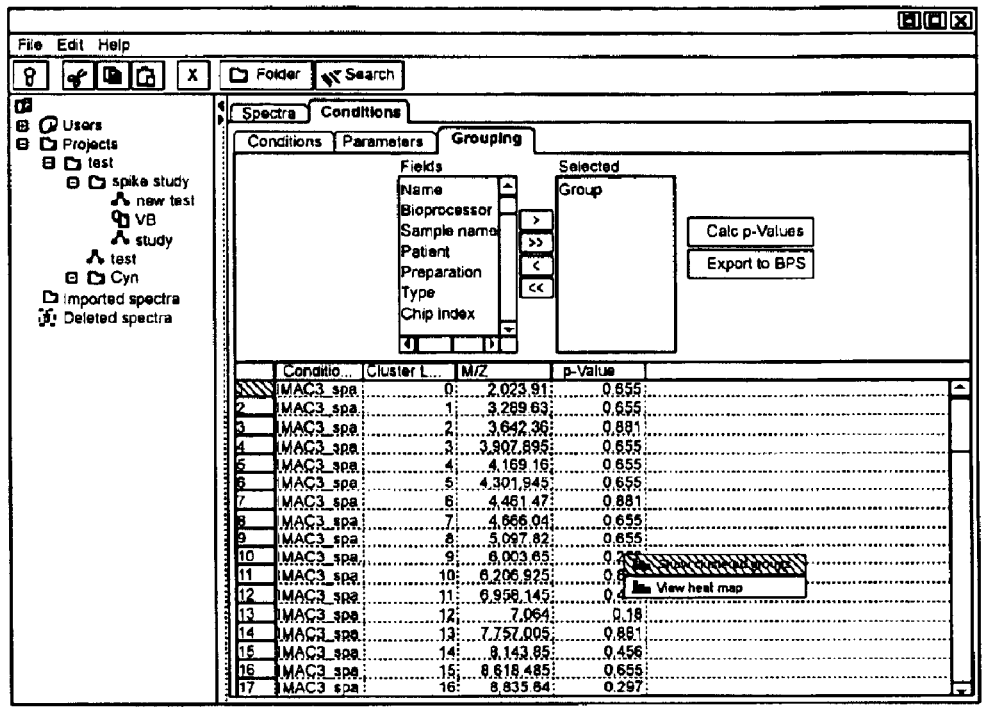
FIG. 12 shows a window where a user can analyze grouped spectra.
Figure 17:
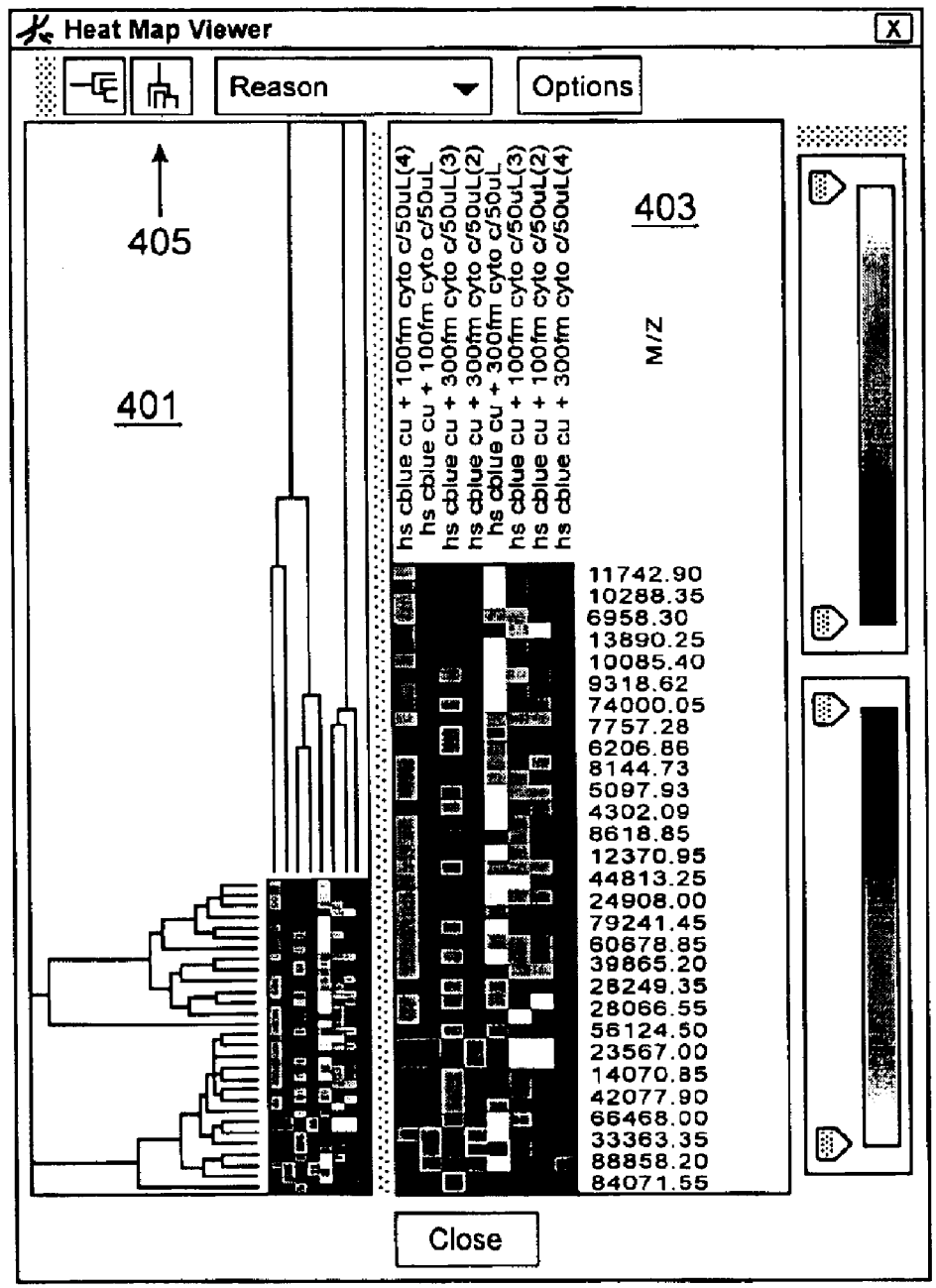
FIG. 17 shows a screenshot showing a heatmap and a dendrogram.

FIG. 12 shows a graphical user interface showing the list of clustered peaks in spectra that may be sorted by any column such as by p- value or by M/Z value. Other visualization tools such as cluster maps and heat maps may show the similarity or dissimilarity between clusters of spectra. Examples of a heatmap 403 and a dendrogram (or cluster map) 401 are shown in FIG. 17. In the dendrogram 401, the lengths of adjacent, paired lines show how similar or dissimilar the spectra are. For example, in some embodiments, the longer a pair of adjacent lines are, the more dissimilar the spectra. Dendrogram buttons 405 may be selected by a user allow the user to cluster spectra by columns or rows (e.g., in a bioprocessor).

Hierarchical clustering and the heat map visualization techniques are described in Eisen, al., "Cluster Analysis and Display of Genome-Wide Expression Patterns", *Proc. Natl. Acad. Sci. USA*, Vol. 95, pp. 14863–14858, December 1998. The algorithm that is described in this paper, however, is different than the one used in embodiments of the invention. In embodiments of the invention, each column in the heat map corresponds to a spectrum, each row a cluster (or a potential marker), and each cell a peak. The color and intensity of each cell is determined by the log normalized intensity of the corresponding peak, which is defined by the equation: log normalized intensity=log intensity−log average intensity. The log normalized intensities are further divided by the largest absolute log normalized intensity in the map. The quotients are finally converted to RGB (red, green, and blue) values, with positive values mapped to red and negative values to green.

Figure 13:
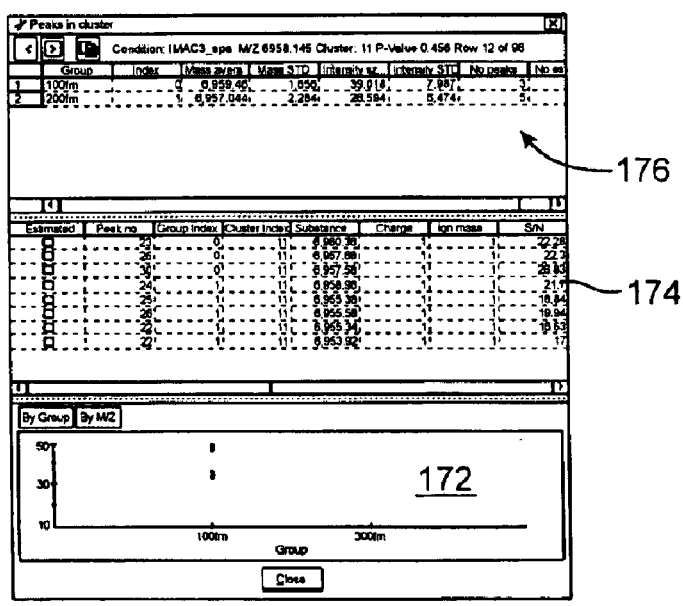
FIG. 13 shows windows showing groups of spectra that are processed according to a differential expression analysis process.

The analysis module may include code for performing a differential expression analysis. For example, FIG. 13 shows a graphical user interface with a first window 176 showing peaks in a peak cluster 11 at a M/Z value of about 6958.145 in two groups of spectra. Group 1 represents a 100 femtomole (fm) group and has three peaks at around 6969.46, and Group 2 represents a 300 femtomole (fm) group and has five peaks around 6,957.044. The data relating to the eight peaks are listed in the table in window 174. The data includes whether or not the peak is an estimated peak, the peak number, the group index, the cluster index, the M/Z value, the charge, the ion mass, and the signal-to-noise ratio (S/N). The plot in window 172 can be used to show peak clusters at 100 fm and 300 fm. As shown in window 172, the peaks cluster differently for the 100 fin samples and the 300 fin samples, thus indicating that the substance that is associated with the M/Z value of about 6958.145 may differentiate the two sample Groups.

Figure 14:
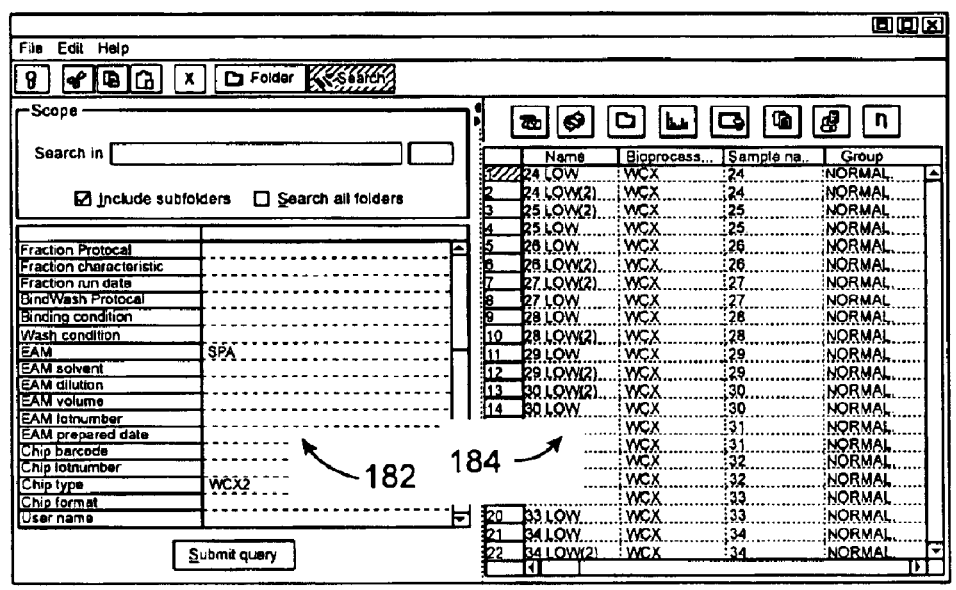
FIG. 14 shows a window where a user can search for spectra according to predetermined values.

FIG. 14 shows a query tool that allows a user to find particular groups of mass spectra. As shown in the window 182 in FIG. 14, the user inputs specific information such as "SPA" for Energy Absorbing Material and "WCX2" for chip type to search for spectra having these values. The results of the query are shown in the window 184 in FIG. 14. As shown in window 184, only mass spectra that are associated with WCX2 and SPA are listed.

Figure 15:
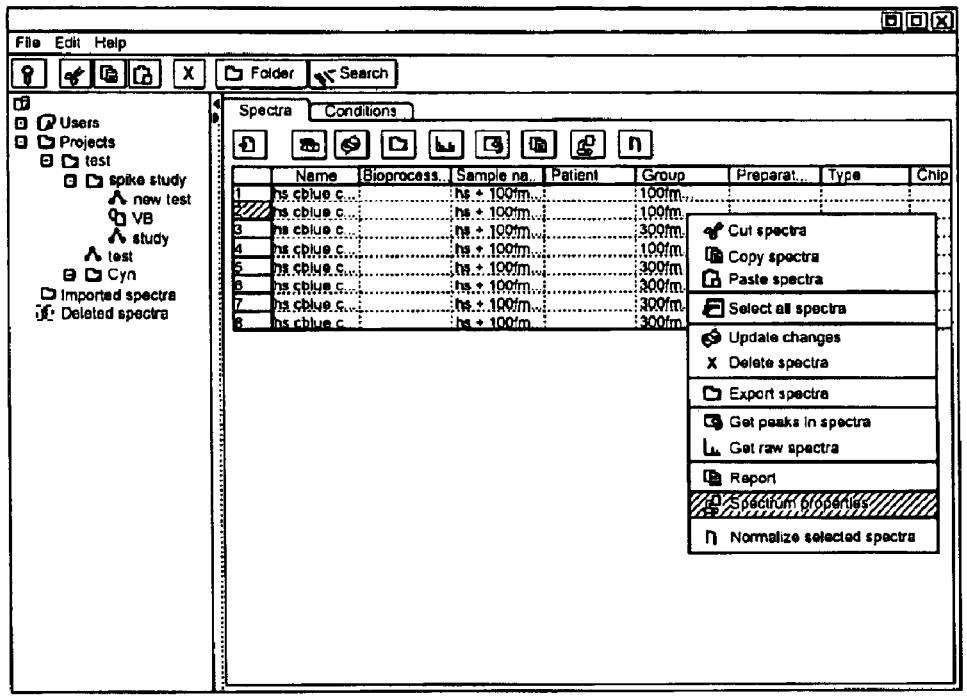
FIG. 15 shows a window where individual spectra can be viewed in greater detail.

FIG. 15 shows a graphical user interface showing a group of spectra and how they can be manipulated in the system. As shown, a user can cut spectra, copy spectra, past spectra, select spectra, update changes, delete spectra, export spectra, get peaks in spectra, get raw spectra, create a report, obtain spectrum properties, and normalize spectra by selecting the appropriate item in the illustrated drop down menu.

Figure 16:
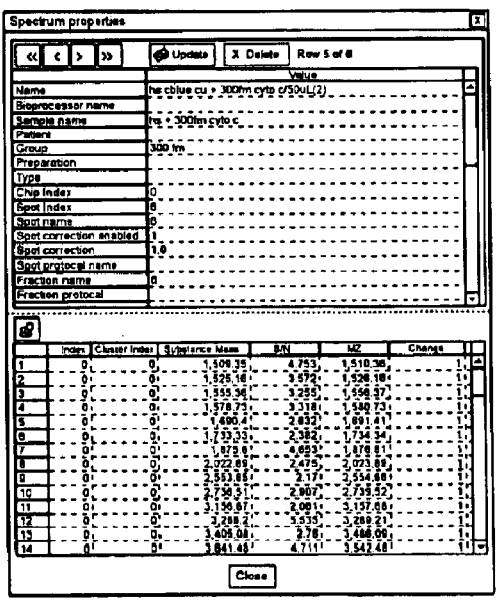
FIG. 16 shows a window with values associated with a particular mass spectrum.

A user may also view the properties of each individual spectrum. For example, FIG. 16 shows a graphical user interface with the particular properties of a particular mass spectrum. As shown, the mass spectrum data is annotated with information such as group, fraction name, etc.

In some embodiments of the invention, the various tables and screens that are described above can be "dynamically altered" for different types of users. For example, FIG. 4 shows a screenshot of a graphical user interface including a table 102 where a user can enter sample data. As shown, the table 102 includes columns. Each column may include different information that may be found in a database such as a relational database. For example, as shown, a "Patient" column includes information identifying a patient. Although the table 102 may be useful for a user that wants to analyze human biological samples, the table 102 may not be useful for a user who wants to enter data relating to plant biological samples into the system.

Conventionally, in order to generate a graphical user interface that displays a screenshot like the one shown in FIG. 4, code for the mapping among relational database elements, programming objects, and the graphical user interface (GUI) is hardcoded in source code. Thus, if one wants to change the data view for the table 102 for a different user, the source code, including code for the object and GUI corresponding to table, would have to be edited for table. This source code would also have to be recompiled, tested, and deployed to all entities that use the software.

In embodiments of the invention, an external configuration file is provided that includes a mapping framework that maps GUI elements to data objects in a database. The data objects may be generic and dynamically extendable. Data for an object are retrieved based on the object's mappings and a GUI is displayed using the GUI elements and the retrieved data.

The data is stored in one or more arrays internally in the generic, dynamically extendable objects, which reside in a database. The mapping framework in the configuration file is used to retrieve the data from the database. For example, a table in a database may have a column for "Patient Name" and a column for "Blood Type". The data table may have two rows. The first row may have "Patient A" as an entry under "Patient Name" and "B-negative" as an entry for "Blood Type". A second row may have "Patient B" as an entry under "Patient Name" and "B-positive" as an entry under "Blood Type". The data in the horizontal row in the table including "Patient A" and "B-negative" may constitute an "object".

As mentioned above, one may want to change the table shown in FIG. 4 so that it is suitable for a variety of different users. For example, one may want to add, delete, or change data displayed in columns. In this case, the changed column with different data and a new table will be generated using the mapping framework without the need for recompilation or any change to the mapping framework. For example, referring to the table 102 shown in FIG. 4, the configuration file would include a mapping framework to generate table 102. The table includes an entry for the "Patient" column. This entry includes a mapping to patient data stored in an internal array in a generic object in the database. If one wants to display different plant data for a biological plant name, an entry replacing "Patient" with "Plant Name" could be included in the configuration file where the entry would include a mapping reference to different, plant data in the database. It is assumed the different data is already included in the database. If it is not, it is understood that the different data could be added to the database or be accessible to the mapping framework. As mentioned above, the mapping framework is configured to read generic objects and map the generic objects to GUI elements. Thus, even if there is a change in the generic object, the framework still can map the changed object to the appropriate GUI elements. Different data are mapped to the GUI elements and displayed. No recompilation is required and the mapping framework does not need to be changed in a substantial way.

Hash tables are also used as a mechanism to store and retrieve data. While hash tables can be used in embodiments of the invention, hash tables require more memory and are slower than the mapping framework described herein. The mapping framework can still use commands typically used to access a hash table, such as getValue(string key) and setValue(String key, Object value), to access data in the arrays of data in the generic objects by converting the commands to commands that get or set a value in the arrays.

While the foregoing is directed to certain preferred embodiments of the present invention, other and further embodiments of the invention may be devised without departing from the basic scope of the invention. Such alternative embodiments are intended to be included within the scope of the present invention. Moreover, the features of one or more embodiments of the invention may be combined with one or more features of other embodiments of the invention without departing from the scope of the invention.

All publications and patent documents cited in this application are incorporated by reference in their entirety for all purposes to the same extent as if each individual publication or patent document were so individually denoted. By their citation of various references in this document Applicants do not admit that any particular reference is "prior art" to their invention.

What is claimed is:

1. A method of processing a plurality of signals, the method comprising:

(a) receiving values associated with a plurality of sample spots on one or more sample chips, wherein the values were entered using graphic elements representing the sample spots on a graphical user interface;

(b) receiving data representing a plurality of signals, wherein the plurality of signals are generated from the sample spots; and (c) automatically annotating each signal in the plurality of signals with a set of values associated with the sample spot from which the signal is generated.

2. The method of claim 1 wherein the signals are mass spectra.

3. The method of claim 1 wherein the method further comprises, before (a):

entering the values associated with the plurality of sample spots into a client computer;

sending the entered values associated with the plurality of sample spots from the client computer to a server computer; and receiving the entered values from the server computer at the client computer.

4. The method of claim 1 wherein the values associated with the plurality of sample spots include at least one selected from the group consisting of sample identification information, a particular sample type, a specific energy absorbing matrix material, a specific wash condition, and a specific chromatography fraction.

5. The method of claim 1 wherein the signals are spectra, and the method further comprises, after (c):

(d) selecting a set of the values;

(e) selecting a group of spectra that have the selected set of values; and (f) analyzing the selected group of spectra selected in (e).

6. The method of claim 5 wherein (f) analyzing the selected group of spectra includes performing a statistical analysis process on the selected group of spectra.

7. The method of claim 5 wherein (f) analyzing the selected group of spectra comprises performing a differential expression analysis or a recursive partitioning process.

8. The method of claim 1 wherein the signals are mass spectra and wherein the method further comprises:

(d) generating the plurality of mass spectra.

9. The method of claim 1 wherein the signals are mass spectra and wherein the method further comprises:

(d) generating the plurality of mass spectra using a surface enhanced laser desorption ionization process.

10. The method of claim 1 wherein the signals are mass spectra and wherein the method further comprises, before (a):

(d) entering the values using the graphic elements on the graphical user interface;

(e) preparing the plurality of sample spots on the one or more sample chips using the entered values in (d); and (e) generating the plurality of mass spectra using a surface enhanced laser desorption ionization process and using the entered values in (d).

11. The method of claim 1 wherein the signals are mass spectra and wherein the method further comprises, before (a):

(d) entering the values using the graphic elements on the graphical user interface;

(e) preparing the plurality of sample spots on the one or more sample chips using the entered values in (d); and (e) generating the plurality of mass spectra using a surface enhanced laser desorption ionization process and using the entered values in (d), wherein (d)–(e) are performed automatically.

12. A computer readable medium comprising:

(a) code for receiving values associated with a plurality of sample spots on one or more sample chips, wherein the values were entered using graphic elements representing the sample spots on a graphical user interface;

(b) code for receiving data representing a plurality of signals, wherein the plurality of signals are generated from the sample spots; and (c) code for automatically annotating each signal in the plurality of signals with a set of values associated with the sample spot from which the signal is generated.

13. The computer readable medium of claim 12 wherein the signals are mass spectra.

14. The computer readable medium of claim 12 wherein the computer readable medium further comprises:

code for entering the values associated with the plurality of sample spots into a client computer;

code for sending the entered values associated with the plurality of sample spots from the client computer to a server computer; and code for receiving the entered values from the server computer at the client computer.

15. The computer readable medium of claim 12 wherein the values associated with the plurality of sample spots include at least one selected from the group consisting of sample identification information, a specific sample type, a specific energy absorbing matrix material, a specific wash condition, and a specific chromatography fraction.

16. The computer readable medium of claim 12 wherein the signals are spectra, and wherein the computer readable medium further comprises:

(d) code for selecting a set of the values;

(e) code for selecting a group of spectra that have the selected set of values; and (f) code for analyzing the selected group of spectra selected in (e).

17. The computer readable medium of claim 16 wherein (f) the code for analyzing the selected group of spectra includes code for performing a statistical analysis process on the selected group of spectra.

18. The computer readable medium of claim 16 wherein (f) the code for analyzing the selected group of spectra comprises code for performing a differential expression analysis or a recursive partitioning process.

19. The computer readable medium of claim 12 further comprising:

(d) code for entering the values using the graphic elements on the graphical user interface;

(e) code for preparing the plurality of sample spots on the one or more sample chips using the entered values in (d); and (e) code for generating the plurality of mass spectra using a surface enhanced laser desorption ionization process and using the entered values in (d).

20. A system for processing mass spectra, the system comprising:

(a) an analytical apparatus; and (b) a digital computer, the digital computer receiving data from the analytical apparatus, the digital computer comprising a computer readable medium including (i) code for receiving values associated with a plurality of sample spots on one or more sample chips, wherein the values were entered using graphic elements representing the sample spots on a graphical user interface;

(ii) code for receiving data representing a plurality of signals, wherein the plurality of signals are generated from the sample spots; and (iii) code for automatically annotating, each signal in the plurality of signals with a set of values associated with the sample spot from which the signal is generated.

21. The system of claim 20 wherein the digital computer is a client computer and wherein the system further comprises:

(c) a server computer in communication with the client computer.

22. The system of claim 20 wherein the signals are mass spectra.

23. The system of claim 20 wherein the values include at least one selected from the group consisting of sample identification information, a particular sample type, a particular energy absorbing matrix material, a specific wash condition, and a specific chromatography fraction.

24. The system of claim 20 further comprising a database in communication with the digital computer, wherein the computer readable medium further comprises:

code for allowing a user to alter a configuration file so that different data is retrieved from the database, and wherein the different data changes the graphical user interface.

25. The system of claim 20 further comprising a database in communication with the digital computer, and wherein the computer readable medium further comprises:

(d) code for entering the values using the graphic elements on the graphical user interface;

(e) code for preparing the plurality of sample spots on the one or more sample chips using the entered values in (d); and (e) code for generating the plurality of mass spectra using a surface enhanced laser desorption ionization process and using the entered values in (d).

* * * * *